United States Patent
Corbett-Jenkins

(10) Patent No.: US 9,326,691 B1
(45) Date of Patent: May 3, 2016

(54) DISPENSABLE SINGLE-USE PROTECTIVE FILM FOR A SPHYGMOMANOMETER

(76) Inventor: Jane Corbett-Jenkins, West Union, SC (US)

( * ) Notice: Subject to any disclaimer, the term of this patent is extended or adjusted under 35 U.S.C. 154(b) by 2066 days.

(21) Appl. No.: 12/313,838

(22) Filed: Nov. 25, 2008

(51) Int. Cl.
*A61B 5/021* (2006.01)
*B32B 5/00* (2006.01)

(52) U.S. Cl.
CPC ............... *A61B 5/02141* (2013.01); *B32B 5/00* (2013.01)

(58) Field of Classification Search
USPC ........... 606/201–203; 600/481, 485, 490–499
See application file for complete search history.

(56) References Cited

U.S. PATENT DOCUMENTS

| | | |
|---|---|---|
| 4,967,758 A | 11/1990 | Masciarotte |
| 5,158,205 A * | 10/1992 | Bodziak et al. ................. 221/51 |
| 5,228,448 A | 7/1993 | Byrd |
| 5,513,643 A | 5/1996 | Suite |
| 5,620,001 A | 4/1997 | Byrd |
| 5,797,851 A | 8/1998 | Byrd |
| 6,585,967 B2 * | 7/2003 | Narang et al. ............. 424/78.31 |

* cited by examiner

*Primary Examiner* — Stacy B Chen
(74) *Attorney, Agent, or Firm* — David L. Banner

(57) ABSTRACT

A pad of disposable protective barrier films for adhesive attached to a blood pressure cuff prior to its placement on a limb of a subject. The barrier film is a thin, non-permeable polymer, typically having a thickness of between approximately 1.0 and 3.0 mil. A portion of the side of the barrier adapted for attachment of the blood pressure cuff is coated with a low tack adhesive. The low tack adhesive holds the barrier in place during installation and use of the blood pressure but allows easy removal and disposal thereof upon completion of the blood pressure measurement. A unique packaging system is provided whereby no adhesive backing strips are required, successive barrier sheets are merely peeled from a stack. In still other embodiments, the barrier or the adhesive may include a germicidal material to further help protect the blood pressure cuff to from germs or other contamination.

13 Claims, 4 Drawing Sheets

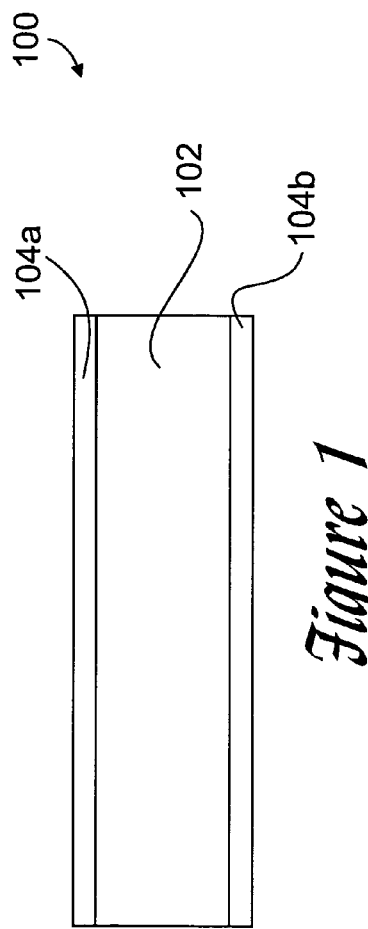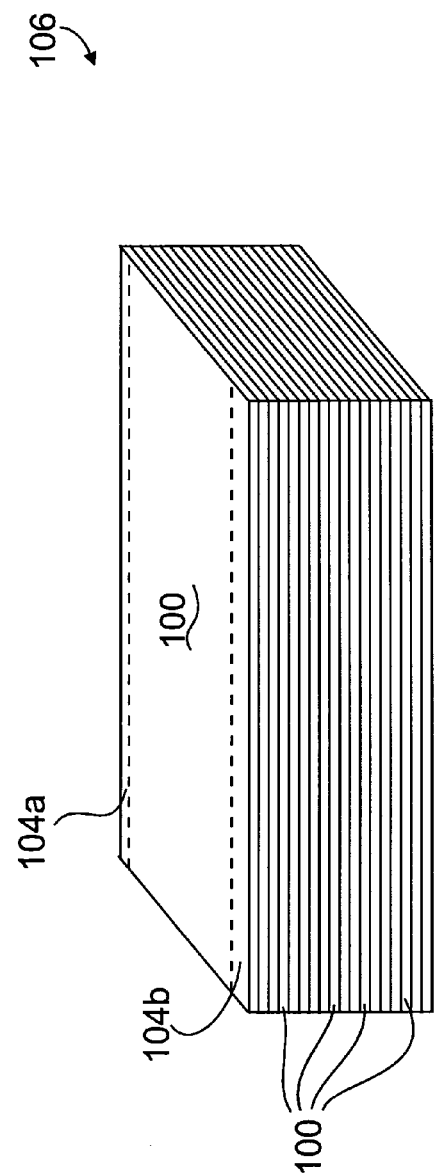

DISPENSABLE SINGLE-USE PROTECTIVE FILM FOR A SPHYGMOMANOMETER

FIELD OF THE INVENTION

The invention pertains to protective devices for use with blood pressure measurement cuffs and the like and, more particularly, to a thin, single-use, adhesively attached barrier film supplied in readily usable dispenser pads.

BACKGROUND OF THE INVENTION

Persons suffering from hypertension or seeking medical care routinely have their blood pressure checked. This procedure is typically performed with a sphygmomanometer, consisting, in part, of an inflatable cuff that is wrapped around the person's limb (e.g., an arm or leg). The cuff is then inflated and deflated while a gauge on the sphygmomanometer is observed to obtain the blood pressure. By acoustically monitoring the flow of blood through a selectively constricted blood vessel, the systolic and diastolic blood pressures may be obtained. This procedure is repeated each time a medical provider desires to take a person's blood pressure. The procedure may be performed manually using a stethoscope or automatically using an instrument specifically designed to automatically measure a subject's blood pressure.

Especially if seeking medical attention for an aliment, a person may have bacteria or other contaminants present on their skin in the region where the cuff is to be placed. In some cases, the subject whose blood pressure is being measured may even have some type of skin diseases, rash, an ulcer, parasitic infestation (e.g., scabies) and/or an abrasion. Such conditions can occur on many areas of the body, including a person's upper and lower limbs. As a result of these conditions, a patient having one of the aforementioned conditions may contaminate a sphygmomanometer and undesirable consequences may result when the sphygmomanometer is used in a multiple patient setting, such as a hospital, clinic, or a physician's office. In particular, if a sphygmomanometer is used on a person having contagious fluids or other contaminants exposed on their skin, those fluids or contaminants may contaminate the cuff on the sphygmomanometer. Subsequent use of the same sphygmomanometer cuff on a second person can possibly transfer such contaminates to the next person and may subsequently cause infection therein.

While protective films are known in the prior art, they are generally packaged in individual packages that require time and effort to open. The individual packaging adds cost to the protective films and requires significant effort by the doctor, nurse, or other practitioner applying the protective film to the sphygmomanometer. Packaging waste adds to the burden of waste disposal.

DISCUSSION OF THE RELATED ART

Various devices that purportedly protect persons from contaminating each other due to the repeated use of a sphygmomanometer have been proposed.

For example, U.S. Pat. No. 4,967,758 for DISPOSABLE COVER/LINER FOR BLOOD PRESSURE MEASURING DEVICES, issued Nov. 6, 1990 to C. Lynn Masciarotte teaches a three-layer, disposable cover liner. The cover/liner is adhered to the blood pressure cuff using a low tack adhesive. Peel-off backings are used to protect the adhesive areas prior its application to the cuff.

U.S. Pat. No. 5,228,448 for PROTECTIVE COVER FOR BLOOD-PRESSURE CUFFS, issued Jul. 20, 1993 to Timothy N. Byrd teaches a two-ply cover that is placed around the appendage of the subject prior to applying the blood pressure cuff thereto.

U.S. Pat. No. 5,513,643 for DISPOSABLE PROTECTION WRAP FOR USE WITH A SPHYGMOMANOMETER, issued May 7, 1996 to Jean M. Suite teaches a protective wrap, secured to the appendage of the subject using Velcro®. The blood pressure cuff is then installed over the SUITE wrap.

U.S. Pat. No. 5,620,001 for UNIVERSAL BLOOD-PRESSURE CUFF COVER, issued Apr. 15, 1997 to Timothy N. Byrd et al. teaches yet another protective cove for a blood pressure cuff. The BYRD et al. apparatus includes a drawstring and adhesive strip for securing the protective cover to itself and around the subject's arm or leg.

U.S. Pat. No. 5,797,851 for MEDICAL BLADDER COVER, issued Aug. 25, 1998 to Timothy N. Byrd teaches a cover releasably sealable to a medical bladder.

None of the foregoing patents, individually, or in any combination, are seen to anticipate or suggest the novel protective blood pressure cuff protective barrier film of the present invention.

It would, therefore, be desirable to provide an inexpensive protective film for a sphygmomanometer that is readily removed from a supply thereof, easily attached to the blood pressure cuff, and readily removed after use without leaving adhesive residue on the blood pressure cuff.

SUMMARY OF THE INVENTION

In accordance with the present invention, there is provided a disposable, protective barrier film designed to be adhesively attached to an inner surface of a blood pressure cuff prior to the cuffs placement on the arm or leg of a subject. The inventive barrier is a thin, non-permeable polymer, typically having a thickness of between approximately 1.0 and 3.0 mil. A portion of the side of the barrier film adapted for attachment of the blood pressure cuff is coated with a low tack adhesive, typically along one or both edges along a major axis thereof. The low tack adhesive holds the barrier film in place during installation and use of the blood pressure cuff but allows easy removal and disposal thereof, typically as regular waste (i.e., without need for disposal as a biohazard) upon completion of the blood pressure measurement. The low-tack adhesive leaves no residue on the blood pressure cuff after use.

A unique packaging system is provided whereby no adhesive backing strips are required, successive barrier sheets are merely peeled from a stack in a manner similar to the well known PostIt® notes provide by 3M Corp. In still other embodiments, one or both of the barrier or the adhesive may include or be treated with an antibacterial, germicidal, antifungal, or other material to further help protect the blood pressure cuff from germs or other contaminates.

It is, therefore, an object of the invention to provide a single use protective barrier film for use with a blood pressure measuring cuff or the like.

It is another object of the invention to provide a single-use protective barrier film for use with a blood pressure measuring cuff formed from a thin, non-permeable polymer.

It is an additional object of the invention to provide a single use protective barrier film for use with a blood pressure measuring cuff that is retained on the blood pressure cuff during use by a low tack adhesive.

It is a further object of the invention to provide a single use protective barrier film for use with a blood pressure measuring cuff that is easily removed after use leaving little or no residue on the blood pressure cuff.

It is another object of the invention to provide a single use protective barrier film for use with a blood pressure measuring cuff that precludes the need for adhesive backing strips on the barrier film's adhesive.

It is a still further object of the invention to provide a single use protective barrier film for use with a blood pressure measuring cuff wherein one or both of the barrier film and the low tack adhesive contain an antibacterial, germicidal, antifungal, or other material or treatment.

It is yet another object of the invention to provide a single use protective barrier film for use with a blood pressure measuring cuff that is provided in sizes adapted to match various standard size blood pressure cuffs.

It is an additional object of the invention to provide a single use protective barrier film for use with a blood pressure measuring cuff that is inexpensive and effective at preventing contamination of a blood pressure cuff.

It is a further object of the invention to provide a single use protective barrier film for use with a blood pressure measuring cuff, which allows accurate blood pressure readings to be quickly taken.

BRIEF DESCRIPTION OF THE DRAWINGS

A complete understanding of the present invention may be obtained by reference to the accompanying drawings, when considered in conjunction with the subsequent detailed description, in which:

FIG. 1 is a top plane view of a barrier film in accordance with the invention;

FIG. 2a is a front, perspective view of a stack of the barrier films of FIG. 1 in a dispensing pad;

DETAILED DESCRIPTION OF THE PREFERRED ENVIRONMENT

The present invention provides a single use, single-layer, impermeable barrier film designed for placement on the inside surface of a blood pressure measurement cuff prior to the cuff's application to a limb of a subject whose blood pressure is to be measured.

Figure 4:
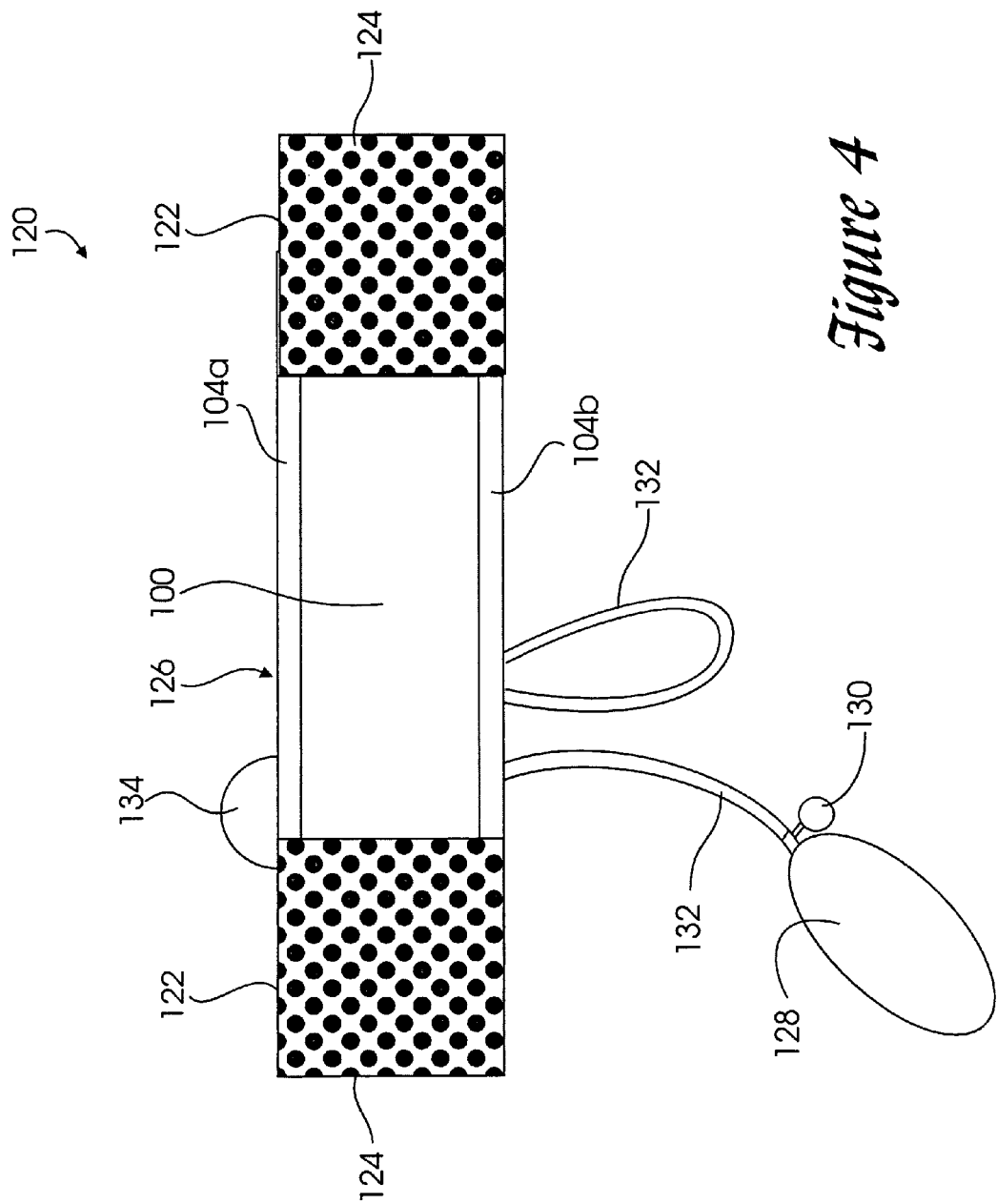
FIG. 4 is a perspective, environmental view of the barrier film of FIG. 1 in its intended operating environment.

Referring first to FIG. 1, there is shown a top plan view of a barrier film in accordance with the present invention, generally at reference number 100. A thin, compliant, protective barrier film 102 has a substantially rectangular form factor sized and configured to fit over and protect the central region 126 (FIG. 4) of a standard blood pressuring apparatus 120 (FIG. 4). Materials suitable for barrier film 102 include non-permeable polymers such as polyethylene, polypropylene, or any other similar polymer. One consideration in choosing a material for barrier film 102 is that the material is ideally latex free to avoid problems with subjects having an allergy to latex. Barrier film 102 ideally has a thickness in the range of approximately 0.001 inch to 0.003 inch (1-3 mils). It is important that the protective barrier film 102 not interfere with the accuracy of any blood pressure measurement made with a sphygmomanometer 120 or other blood pressure measurement apparatus, not shown. Experiments have shown than an excessive film thickness may cause up to a 10 point inaccuracy in blood pressure readings. A 10 point inaccuracy may falsely identify a subject as hypertensive when indeed the subject is not hypertensive. Conversely, a truly hypertensive subject in need of treatment may fail to be identified because of inaccuracy imparted by barrier film 102 if the barrier film 102 is too thick. However, it will be recognized that other film compositions or thicknesses may also be chosen and the invention is not considered limited to that particular materials or film thicknesses chosen for purposes of disclosure. Rather the invention is seen to include any suitable polymeric material provided in a suitable thickness that does not impart significant inaccuracy to a blood pressure measurement made with barrier film 102 in place on the sphygmomanometer 120.

Barrier film 102 is provided with adhesive bands 104a, 104b disposed along the edges parallel to the major axis thereof. While adhesive bands 104a, 104b are shown for purposes of disclosure, it will be recognized that other adhesive locations and/or patterns may be chosen to meet a particular operating circumstance or environment.

Adhesive bands 104a, 104b consist of a low tack adhesive. Low tack adhesives are well known to those of skill in the art and are not further described herein. Any low-tack adhesive having sufficient adhesion to secure barrier film 102 to the inner surface 126 of blood pressure cuff 120 before and during a blood pressure measurement and yet be readily removed after use may also be used. Consequently, the invention is not considered limited to the particular adhesive chosen for purposes of disclosure. However, it is important that the adhesive not remain on inner surface of central region 126 following removal of barrier film 102. Any accumulation of adhesive on an inner surface of blood pressure cuff 120 may cause dirt and/or other contaminants to stick to the adhesive-contaminated region causing the blood pressure cuff 120 to become unsightly and/or unsanitary. The invention covers any and all suitable adhesives meeting the necessary criteria as described hereinabove.

While adhesive bands 104a, 104b applied along edges parallel to a major axis of thin film 102 have been chosen for purposes of disclosure, it will be recognized that other adhesive orientations, for example, adhesive bands, not shown applied to one or both edges of thin film 102 perpendicular to the major axis thereof. Consequently, the invention is not limited a particular edge or edges to which an adhesive is applied.

Referring now also to FIG. 2a, there is shown a front, perspective view of a stack of barrier films 100 in a dispensing configuration, generally at reference number 106. When needed, the top barrier film 100 may readily be removed from the top of stack 106 and positioned on blood pressure cuff 120 without need for unpackaging an individually-wrapped protective device of the prior art.

Figure 2B:
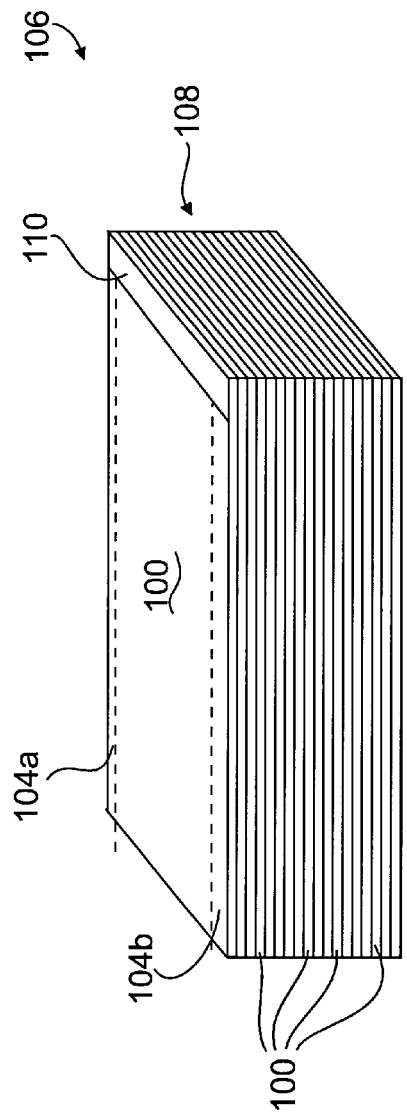
FIGS. 2b and 2c are a front, perspective views of a stack of the barrier films of FIG. 2a with modified adhesive patterns to facilitate removal.
Figure 2C:
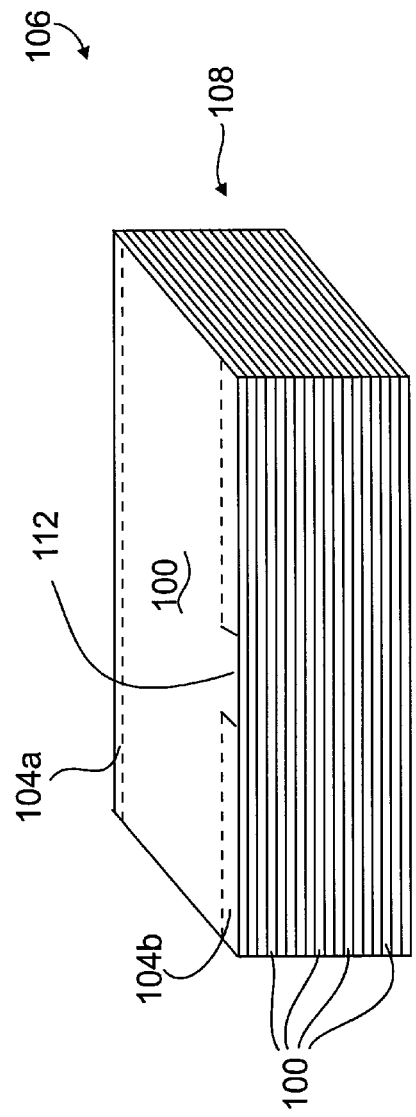

It will be recognized that the adhesive strips 104a, 104b may be modified to facilitate removal of a barrier film 100 from stack 106. Referring now also to FIGS. 2b and 2c, there are shown two possible adhesive pattern variations. In FIG. 2b, adhesive strips 104a and 104b are shortened to leave an adhesive-free region 110 adjacent end 108 of stack 106. In FIG. 2c, adhesive strip 104b is interrupted at approximately a midpoint along a major axis of stack 106, leaving and adhesive-free region 112.

Figure 3:
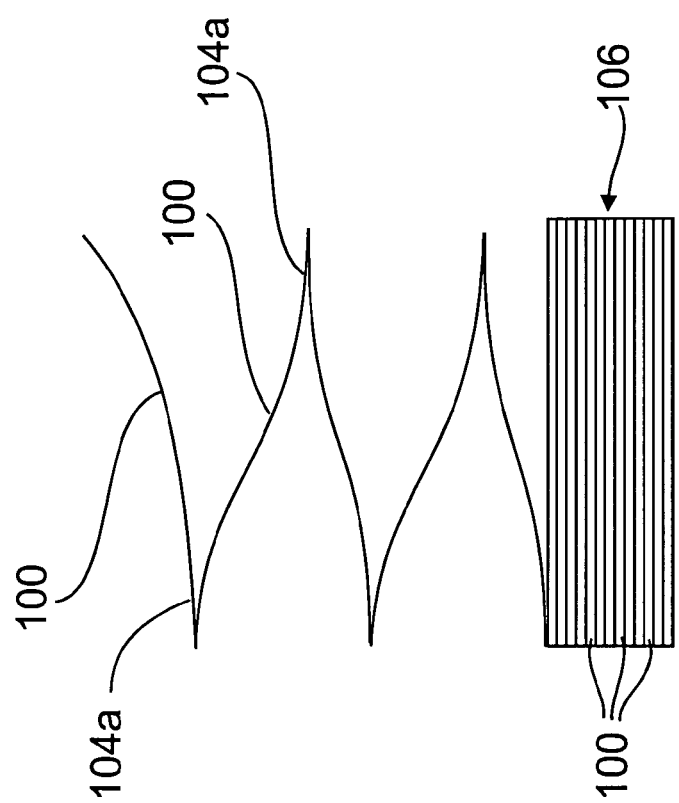
FIG. 3 is a side, elevational view of a fan-fold packaging configuration for the barrier film of FIG. 1.

In alternate embodiments, barrier sheets 100 may be fan-folded as shown in FIG. 3. It will be recognized by those of skill in that art that numerous other packaging strategies and/or configurations are possible. Therefore, the invention is not considered limited to the embodiments chosen for purposes of disclosure. Rather, the invention includes any and all other possible adhesive patterns and packaging configurations.

Referring now to THE FIG. 4, there is shown a perspective, environmental view of a typical blood pressure cuff 120 with the protective barrier film 100 of the present invention installed on an inside surface at a central region 126 thereof. Blood pressure cuff 120 has a central region 126 and two end regions 122 disposed along a major axis of blood pressure cuff 120 at either side of the central region 126. One or both end regions 122 typically have hook and loop fastening material 124 (e.g., Velcro®) installed thereupon. It will be recognized that other suitable fastening systems may be used to secure the blood pressure cuff 120 around the limb of a person, not shown, the fastening system forming no part of the present invention.

A compliant bulb 128 is connected by tubing 132 to an internal bladder, not shown, disposed in central region 126 of blood pressure cuff 120. A release valve 130 is provided to controllably release pressure from the internal bladder. A pressure gauge 134 is disposed on a front surface, not shown, of blood pressure cuff 120.

Barrier film 100 is adhered to the inner surface of central region 126 by low tack adhesive 104a, 104b shown disposed along the edges of barrier film 100.

In use, barrier film 100 is removed from stack 106 (FIG. 2a) and adhered to the inner surface (i.e., the surface that will be toward the skin of a subject, not shown, whose blood pressure is to be measured) of central region 126. Once barrier film 100 is in place, blood pressure cuff 120 is placed around a suitable appendage, normally the arm or leg, not shown, of the subject, not shown. The blood pressure reading is taken using a technique well known to those of skill in the medical arts. The blood pressure cuff 120 is then removed from the subject's appendage or limb and barrier film 100 is removed and discarded. Typically, barrier film 100 may be discarded as regular waste (i.e., used barrier films 100 need not be treated as biohazardous waste).

It will be recognized that blood pressure cuffs 120 are provided in a wide range of sizes ranging from those suitable for use with a premature baby to those large enough to encircle the upper leg or thigh of an overweight adult. Consequently, barrier films 100 of the instant invention may be provided in a range of sizes suitable for each size of blood pressure cuff.

The consistent use of the barrier film 100 in accordance with the present invention has the added benefit that the blood pressure cuff 120 remains cleaner, thus providing a longer effective service life. This is because the oils present on the skin of subjects are kept away from the fabric surface of the inner surface of central region 126. The added service life of blood pressure cuff 100 more than offsets the cost of barrier films 100.

In other embodiments, barrier film 100 may contain or be treated with a germicidal, antifungal, or other chemical or medicinal treatment, not shown, Such treatments are believed well known to those of skill in the art and are not further discussed herein.

In still other embodiments, the novel barrier films 100 may be provided in a continuous roll and cut to length at the time of dispensing.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A plurality of protective barrier films for covering a central region of a blood pressure cuff, comprising:
   a) a plurality of thin, single-layer films adapted and configured for placement against an inner surface of a central region along a major axis of a blood pressure cuff; and
   b) adhesive placed on a portion of a single surface of each of said thin films, said single surface being adapted for releasable contact with said inner surface of said central region of said blood pressure cuff;
   each of said plurality of thin films being placed against another in a padded dispensing configuration whereby an upper most one of said plurality of thin films is readily removable from said pad.

2. The plurality of protective barrier films for a blood pressure cuff as recited in claim 1, wherein each of said plurality of thin films is impermeable.

3. The plurality of protective barrier films for a blood pressure cuff as recited in claim 2, wherein each of said plurality of thin films comprises a polymer film.

4. The plurality of protective barrier films for a blood pressure cuff as recited in claim 3, wherein each of said thin films comprises a polymer film having a thickness in the range of approximately 0.001 inch to 0.003 inch.

5. The plurality of protective barrier films films for a blood pressure cuff as recited in claim 1, wherein said adhesive is disposed adjacent at least one edge of each of said thin films parallel to a major axis thereof.

6. The plurality of protective barrier films for a blood pressure cuff as recited in claim 5, wherein said adhesive is disposed adjacent both edges of said thin film parallel to a major axis thereof.

7. The plurality of protective barrier films for a blood pressure cuff as recited in claim 1, wherein said adhesive is disposed adjacent at least one edge of each of said thin films substantially perpendicular to a major axis thereof.

8. The plurality of protective barrier films films for a blood pressure cuff as recited in claim 1, wherein at least one of said thin films is absent a backing membrane in a region containing said adhesive.

9. The plurality of protective barrier films for a blood pressure cuff as recited in claim 1, wherein at least one of said plurality of thin films comprises a germicidal material.

10. The plurality of protective barrier films for a blood pressure cuff as recited in claim 1, wherein said adhesive comprises at least one material chosen from the group: an antibacterial material, a germicidal material, and an antifungal material.

11. The plurality of protective barrier films for a blood pressure cuff as recited in claim 1, wherein said packaging configuration comprises a fan-fold configuration.

12. A method of preventing contamination of a blood pressure cuff, the steps comprising:
   a) providing the plurality of protective barrier films of claim 1;
   b) removing one of said thin films from said pad;
   c) placing said removed thin film over an inner surface of a central region of a blood pressure cuff such that said thin film substantially completely covers said central region of said inner surface;
   d) using said blood pressure cuff to make a blood pressure assessment of a subject; and e) removing and discarding said thin film from said inner surface of said central region of said blood pressure cuff.

13. A method of preventing contamination of a blood pressure cuff as recited in claim 12, wherein at least one of said plurality of thin films comprises at least one material chosen from the group: an antibacterial material, a germicidal material, and an antifungal material.

* * * * *